United States Patent [19]

Harris, III et al.

[11] Patent Number: 4,865,837
[45] Date of Patent: Sep. 12, 1989

[54] ALDOXIME-SUBSTITUTED TRIAZOLIUM COMPOUNDS USEFUL IN THE TREATMENT OF POISONING BY PHOSPHORUS-CONTAINING CHEMICALS

[75] Inventors: Ralph N. Harris, III, Redwood City, Calif.; Clifford D. Bedford, Silver Spring, Md.; Duane E. Hilmas, Worthington, Ohio; Robert A. Howd, San Jose, Calif.; Richard A. Kenley, Libertyville, Ill.; Gary A. Koolpe, Mountain View, Calif.

[73] Assignee: SRI International, Menlo Park, Calif.

[21] Appl. No.: 78,921

[22] Filed: Jul. 28, 1987

[51] Int. Cl.[4] .................... C07C 249/08; A61K 31/41
[52] U.S. Cl. ....................................... 424/10; 514/383; 548/269
[58] Field of Search .................. 548/269; 514/383; 424/10

[56] References Cited

U.S. PATENT DOCUMENTS 3,773,775  11/1973  Hagedorn ........................... 548/269
3,852,294  12/1974  Hagedorn ........................... 548/269

FOREIGN PATENT DOCUMENTS 7636169  3/1980  France .

OTHER PUBLICATIONS

C. F. Wilkinson et al, "Structure-Activity Relationships in the Effects of 1-Alkylimidazoles on Microsomal Oxidation In Vitro and In Vivo", *Biochemical Pharmacology*, vol. 23, 1974, pp. 2377-2386.

Irwin B. Wilson et al, "A Specific Antidote Against Lethal Alkyl Phosphate Intoxication, V. Antidotal Properties", *Archives of Biochemistry and Biophysics*, vol. 69, 1957, pp. 468-474.

M. R. Atkinson et al, "Triazoles, Part II, N-Substitution of Some 1:2:4–Triazoles", *Journal of the Chemical Society*, 1954, pp. 141-145.

Clifford D. Bedford et al, "Structure-Activity Relationships for Reactivators of Organophosphorus-Inhibited Acetylcholinesterase: Quaternary Salts of 2-[(Hydroxyimino)Methyl]Imidazole", *Journal of Medicinal Chemistry*, vol. 27, No. 11, 1984, pp. 1431-1438.

Mario Grifantini et al, "Structure-Activity Relationships in Reactivators of Organophosphorus-Inhibited Acetylcholinesterase V: Quaternary Salts of Hydroxyiminomethylimidazoles", *Journal of Pharmaceutical Sciences*, vol. 61, No. 4, Apr. 1972, pp. 631-633.

M. Mar Herrador et al, "Reactivators of Organophosphorus-Inhibited Acetylcholinesterase, 1, Imidazole Oxime Derivatives", *Journal of Medicinal Chemistry*, vol. 28, No. 1, 1985, pp. 146-149.

Palle E. Iversen et al, "Preparation of 2–Imidazole- and 2–Thiazolecarbaldehydes", *Acta Chemica Scandinavica*, vol. 20, No. 10, 1966, pp. 2649-2657.

Edward J. Poziomek et al, "Pyridinium Aldoximes", *Journal of Organic Chemistry*, vol. 23, May 1958, pp. 714-717.

*Primary Examiner*—John M. Ford
*Attorney, Agent, or Firm*—John P. Taylor

[57] ABSTRACT

A therapeutically effective class of low toxicity aldoxime-substituted trazolium derivatives is disclosed which is effective in the treatment of living species poisoned by organophosphorus chemicals which inactivate the enzyme acetylcholinesterase. In vivo administration of therapeutically effective amounts of these low toxicity aldoxime-substituted triazolium derivatives has been found to save mice having inhibited acetylcholinesterase due to injection with lethal dosages of Soman.

6 Claims, No Drawings

ALDOXIME-SUBSTITUTED TRIAZOLIUM COMPOUNDS USEFUL IN THE TREATMENT OF POISONING BY PHOSPHORUS-CONTAINING CHEMICALS

BACKGROUND OF THE INVENTION

The invention described herein was made in the course of work under contracts DAMD17-82-C-2194 and DAMD17-85-C-5154 with the Department of Defense.

1. Field of the Invention

This invention relates to particular aldoxime salts useful in the treatment of poisoning by certain chemicals containing phosphorous. More particularly, this invention relates to particular compounds comprising substituted 1,2,4-triazolium-3-aldoxime salts.

2. Description of the Related Art

Certain organic chemicals containing phosphorous including some agriculture chemicals (pesticides) such as parathion, chemical warfare agents such as Soman and Tabun, and other organo-phosphorous chemicals such as ethyl-p-nitrophenyl methylphosphonate (EPMP) attack the central nervous system of animals, including humans, and inactivate the body's naturally produced enzyme acetylcholinesterase, sometimes also called cholinesterase. This enzyme is used in living organisms to break down the naturally produced acetylcholine released by cholinergic neurons as a part of normal function of the autonomic nervous system.

Administration of the drug atropine has long been used as a treatment for the effects of such poisoning. For example, it increases the heart rate which would otherwise be decreased by an excess of acetylcholine in the system due to inactivation of the acetylcholinesterase enzyme which normally would immediately break down the acetylcholine. However, atropine cannot restore activity to (reactivate) the inhibited acetylcholinesterase. Other drugs, therefore, are conventionally administered with atropine to reactivate the acetylcholinesterase enzyme. Such drugs include toxogonin and 2-PAM, which contains the active agent 2-(hydroxyimino)methyl-1-methylpyridinium chloride.

Hagedorn U.S. Pat. Nos. 3,773,775 and 3,852,294 describe the use of (hydroxyimino)methylpyridinium compounds for treating and alleviating the symptoms of poisoning caused by exposure to phosphorus-containing pesticides and war gases.

Poziomek et al., in an article entitled "Pyridinium aldoximes" published in the Journal of Organic Chemistry, Vol. 23 in 1958 at pp. 714–717, describe the preparation and testing of a number of pyridinium aldoximes including 1,1'-polymethylenebis(4-formylpyridinium bromide) dioximes and N-substituted 2- and 4-formylpyridinium halide oximes and report that the bis-quaternary dioximes are active as chemotherapeutic agents in the treatment of acetylcholinesterase poisoning in experimental animals.

Wilson et al., in "A Specific Antidote Against Lethal Alkyl Phosphate Intoxification. V. Antidotal Properties", published in the Archives of Biochemistry and Biophysics, Vol. 69, in 1957 at pp. 468–474, discusses the effects of pyridine-2-aldoxime methiodide as an in vitro reactivator of alkyl phosphate-inhibited acetylcholinesterase.

However, these pyridine-based chemical agents are not always effective in reactivating the acetylcholinesterase enzyme, particularly when the body has been exposed to a large dosage of the acetylcholinesterase enzyme-inactivating chemical. Furthermore, the synthesis of at least some pyridinebased compounds requires the use of the known carcinogen bischloromethyl ether and a major requirement in the use of these oxime therapeutics is to guarantee to the Food and Drug Administration (FDA) in IND and NDA reports that no carcinogenic materials remain in the final product.

It was also found that attempts to produce some oxime-substituted pyridine-based chemicals resulted in the formation of derivatives which were relatively unstable and could not, therefore, be stored very long, which made their potential use as therapeutic agents dubious at best.

It is known that alkylimidazoles have therapeutic effects as treatment agents. Wilkinson et al., in "Structure-Activity Relationships in The Effects of 1-alkylimidazoles On Microsomal Oxidation In Vitro And In Vivo", published in the Journal of Biochemical Pharmacology, Vol. 23 in 1974 at pp. 2377–2386, describes the biological activities of a number of 1-alkyl substituted imidazole compounds including activity as inhibitors of drug oxidation and potentiators of barbiturate sleeping time in mammals.

The preparation of N-substituted 1,2,4-triazoles has been reported in the literature. Atkinson et al., in an article entitled "Triazoles. Part II.* N-Substitution of Some 1:2:4-Triazoles", published in the Journal of the Chemical Society in 1954 at pp. 141–145, disclose the formation of various 1,2,4-triazoles including derivatives of 3,5-dimethyl-1,2,4-triazole formed by alkylation.

The use of (hydroxyimino)methylimidazoles (aldoxime-substituted imidazolium derivatives) has also been explored for the treatment of organo-phosphorus poisoning in comparison to the pyridine-based 2-PAM standard treatment agent. Grifantini et al., in an article entitled "Structure-Activity Relationships in Reactivators of Organophosphorus-Inhibited Acetylcholinesterase V: Quaternary Salts of Hydroxyiminomethylimidazoles", published in the Journal of Pharmaceutical Sciences, vol. 64, No. 4, in 1972 at pp. 631–633, describes the effectiveness of quaternary salts of some derivatives of 2-(hydroxyimino)methylimidazole and 5-(hydroxyimino)methylimidazole on the reactivation of organophosphorus-inhibited acetylcholinesterase when inhibited by diethylphosphoryl and diisopropylphosphoryl groups. The reactivities of the two 2-(hydroxyimino)methylimidazole derivatives tested were respectively reported as a half and a fourth of that of 2-(hydroxyimino)methyl-1-methylpyridinium iodide (2-PAM).

Herrador et al., in an article entitled "Reactivators of Organophosphorus-Inhibited Acetylcholinesterase. 1. Imidazole Oxime Derivatives", published in the Journal of Medicinal Chemistry, Vol 28, in 1985 at pp. 146–149, discloses the synthesis and biological screening of 1-aryl(alkyl)-4-[(hydroxyimino)-methyl]-3-methylimidazolium iodides and 1-aryl(alkyl)-4-[(hydroxyimino)methyl]-3-methyl-2-(methylthio)-imidazolium iodides as potential reactivators of organophosphorus-inhibited acetylcholinesterase. All materials tested were reported as weak reactivators with the best ones said to be about two times less active than 2-PAM.

Bedford et al, in an article entitled "Structure-Activity Relationships for Reactivators of Organophosphorus-Inhibited Acetylcholinesterase: Quaternary Salts of 2-[(Hydroxyimino)methyl]imidazole" coauthored by some of us and published in the Journal of Medicinal Chemistry, Vol. 27, No. 11, 1984, at pages 1431–1438, discussed the in vitro testing of 1-methyl-2-(hydroxyimino)methyl-3-(alkoxy or aralkoxy)methyl-imidazolium chloride salts as reactivators of eel acetylcholinesterase inhibited by 3,3-dimethyl-2-butyl methylphosphonofluoridate (GD or Soman).

While the 2-[(hydroxyimino)methyl]imidazolium salts reported in this article have been subsequently found to be sufficiently effective in the treatment of acetylcholinesterase inhibited by organo-phosphorus compounds to save as high as 60% of mice injected with a lethal dose ($LD_{50}$) of Soman, it has also been found that the toxicity of such compounds is also quite high as determined by the low value of the $LD_{50}$ of the antidotal compound, i.e., the lower the amount of the antidotal compound which is lethal to 50% of the species to which it is administered, the more toxic the compound. When the antidotal compound has a low $LD_{50}$, less of it can be safely administered to the species as an antidote to the organo-phosphoric chemical.

It, therefore, would be beneficial to provide a class of low toxicity, stable aldoxime-substituted azolium derivatives which would be more effective than standard pyridine-based treatment agents such as 2-PAM in the reactivation of the acetylcholinesterase enzyme and which would be capable of being produced without the use of precursors which are known carcinogens. Surprisingly, despite the teachings of the prior art, we have discovered a class of stable aldoxime-substituted triazolium derivatives which are more effective than 2-PAM in the reactivation of acetylcholinesterase and yet have lower toxicity than the previously reported aldoxime-substituted imidazolium compounds.

SUMMARY OF THE INVENTION

It is, therefore, an object of this invention to provide particular low toxicity aldoxime-substituted triazolium compounds which are therapeutically effective in countering the inactivation of acetylcholinesterase by exposure of living species to toxic organo-phosphoric chemicals.

It is another object of the invention to provide a therapeutically effective treatment of living species in countering the inactivation of acetylcholinesterase enzyme by exposure to toxic organophosphoric chemicals.

It is yet another object of the invention to provide a therapeutically effective treatment of living species to counter the inactivation of acetylcholinesterase enzyme by exposure to toxic organophosphoric chemicals by the administration of a therapeutically effective amount of a low toxicity aldoxime-substituted triazolium compounds.

These and other objects of the invention will be apparent from the following description.

DETAILED DESCRIPTION OF THE INVENTION

In accordance with the invention, certain low toxicity aldoxime-substituted triazolium compounds are provided which are effective in the treatment of living species poisoned by organo-phosphoric chemicals which inactivate the enzyme acetylcholinesterase. These compounds have been found to be effective in the treatment of living species having inhibited acetylcholinesterase due to poisoning by toxic organo-phosphorus compounds. More particularly, such compounds have been found to be effective in saving mice from otherwise lethal dosages of Soman.

By the use of the terms "effective" and "effective amounts" when used herein to describe, for example, the in vivo treatment of living species to counter the inactivation of the acetylcholinesterase enzyme, is meant an amount of an aldoxime-substituted azolium compounds which will be at least as effective as an equivalent dosage of 2-PAM, and preferably more effective than the equivalent amount of 2-PAM as measured in the number of mice surviving in vivo testing as will be discussed below.

By use of the term "low toxicity" is meant an aldoxime-substituted triazolium compounds having an $LD_{50}$ of at least 0.1 millimoles/kg., preferably at least about 0.25 millimoles/kg., and most preferably at least about 1.0 millimoles/kg., i.e., at least 0.1 millimoles, preferably at least 0.25 millimoles, and most preferably at least 1.0 millimoles, of the compound must be administered per kilogram body weight of the living species to result in 50% fatalities.

The aldoxime-substituted triazolium compounds of the invention comprise derivatives of quaternary 3-(hydroxyimino)methyl-1,4-($RR_1$)trisubstituted 1,2,4-triazolium salts having the formula:

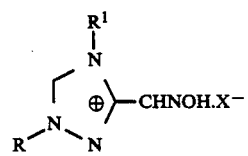

Formula I wherein:

R is selected from the class consisting of alkyl, alkenyl, and alkynyl;

$R_1$ is selected from the class consisting of alkyl, alkenyl, alkynyl, aralkyl, and aryl wherein any of the substituents may be functionalized with one or more substituents selected from the class consisting of hydrogen, nitro, cyano, azido, carboxy, carboalkoxy, carbamoyl, halogen, ether, thioether, sulfoxide, sulfone, sulfonic acid, sulfonamide, amino, substituted aminos, and amido; and X is a therapeutically acceptable anion selected from the class consisting of a salt of an inorganic acid and a salt of an organic acid.

By the term "functionalized with" is meant that the radical, where chemically possible, may have a further substitute group thereon selected from the list of substituents.

Examples of therapeutically acceptable salts of inorganic and organic acids used in forming the anion X include halide, sulfate, phosphate, tartrate, citrate, alkanesulfonate, arylsulfonate, perfluoroalkanesulfonate, succinate, acetate, malate, fumerate, or salicylate.

Particularly preferred triazolium salts of the Formula I type include:

Compound 1: 1,4-dimethyl-3-(hydroxyimino)methyl-1,2,4-triazolium chloride;

Compound 2: 1-benzyl-3-(hydroxyimino)methyl-4-methyl-1,2,4-triazolium chloride; and Compound 3: 3-(hydroxyimino)methyl-1-methyl-4-(2'-methylsulfonyl-1'-ethyl)-1,2,4-triazolium chloride.

While we do not wish to be bound by any theory of how the compounds of the invention operate to counter the inactivation of acetylcholinesterase by organo-phosphorus chemicals, it is believed that the compounds of the invention may actually reactivate the acetylcholinesterase rather than merely treat the effects of such inactivation as does, for example, the drug atropine. In any event the use of the term "counter" herein is intended to mean that the compounds of the invention have an effect on the living species previously poisoned with an organo-phosphorus compound and then treated which is similar to the effect which would be expected if the acetylcholinesterase was reactivated.

The compounds of Formula I may be processed to all forms of preparations customary for pharmaceutical purposes. For example, pills, tablets, dragees, solutions, emulsions, syrups, and injection solutions can be produced therefrom. Suitable pharmaceutical excipients are those organic substances which are adapted for parenteral, enteral, or topical application and which do not react with the novel compounds, such as water, vegetable oils, polyethylene glycols, gelatin, lactose, amylose, magnesium stearate, talc, Vaseline, cholesterol,, etc. Especially suitable for parenteral application are solutions, preferably oily or aqueous solutions, as well as suspensions or emulsions. For enteral application, tablets or dragees may be employed. For topical applications salves or creams which can be sterilized or mixed with auxiliary substances such as preservatives, stabilizers, or wetting agents, or salts for influencing the osmotic pressure, or with buffered substances are preferred.

The compound may be administered in dosages which range from 0.05 grams to 20 grams, depending upon the body weight of the living species, and can be administered as a single dose.

Each of the pharmaceutically active compounds of the invention may be incorporated, for oral administration, in a tablet as the sole active ingredient. A typical dosage tablet is constituted by from 1 to 3 wt.% binder, e.g., tragacanth; from 0.25 to 10 wt.% lubricant, e.g., talcum or magnesium stearate; an average dosage of active ingredient; and the balance consisting of a filler material, e.g., lactose. Tablets may be prepared using standard tableting techniques such as well known to those skilled in the art, employing the necessary amounts of conventional granulating liquids, e.g., alcohol SD-30 and purified water. An exemplary tableting formulation for the instant active compounds is as follows:

| Ingredient | Parts by Weight |
| --- | --- |
| Compounds of Formula I or II | 50 |
| Tragacanth | 2 |
| Lactose | 39.5 |
| Corn Starch | 5 |
| Talcum | 3 |
| Magnesium Stearate | 0.5 |
| Alcohol SD-30 q.s. | |
| Purified Water q.s. | |

PREPARATION OF FORMULA I COMPOUNDS

Formula I type aldoxime-substituted 1,2,4-triazole compounds may be prepared by first forming a 1-substituted-1,2,4-triazole using the teachings of the aforementioned Atkinson et al article to provide the following precursor:

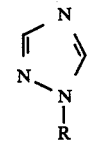

1-substituted-1,2,4-triazole Precursor wherein R, as discussed previously, is selected from the class consisting of alkyl, alkenyl, and alkynyl.

This precursor is converted to the carbaldehyde form using the teachings of the previously mentioned Atkinson et al article to achieve the following compound:

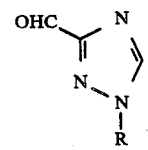

1-alkyl-3-formyl-1,2,4-triazole

The carbaldehyde precursor is then subjected to an oximation reaction procedure by reacting it with hydroxylamine hydrochloride and alkali such as NaOH or NaHCO$_3$ in an alcoholic solvent at a temperature of 65° to 80° C. for a period of 2 hours to produce the following precursor:

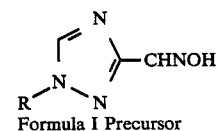

Formula I Precursor

The formula I aldoxime-substituted 1,2,4-triazole compounds is prepared from this precursor by reacting the precursor with a compound having the formula R$_1$CH$_2$X wherein R$_1$, as previously discussed above, is selected from the class consisting of alkyl, alkenyl, alkynyl, aralkyl, and aryl wherein any of the substituents may be functionalized with one or more substituents selected from the class consisting of hydrogen, nitro, cyano, azido, carboxy, carboalkoxy, halogen, ether, thioether, sulfoxide, sulfone, sulfonic acid, sulfonamide, amino, and carbamoyl; and X is a therapeutically acceptable anion selected from the class consisting of a salt of an inorganic acid and a salt of an organic acid.

The following examples which describe the synthesis of a number of compounds of the invention and the in vivo testing of compounds of the invention, as well as 2-PAM, in mice injected with lethal doses of Soman will serve to further illustrate the invention.

EXAMPLE 1

To a stirring solution of 14.0 grams of 1-methyl-1,2,4-triazole in 100 ml of dry tetrahydrofuran and 200 ml of anhydrous diethyl ether under an argon atmosphere and cooled at −50° to −40° C. was added dropwise 0.183 moles of n-butyllithium in hexane. After stirring for 1.5 hours, the mixture was cooled to −75° to −70° C., and there was added 19.3 ml of dry dimethylformamide in one portion. The mixture was allowed to warm to room temperature and stirred for 12–14 hours whereupon there was added dropwise 125 ml of 4N hydrochloric acid. The layers were separated, and the organic layer was washed with two 20 ml portions of 4N hydrochloric acid. The combined aqueous layers were then basified to pH 9.0 with sodium carbonate and extracted with six portions of dichloromethane. The combined extracts were dried and evaporated to give crude 3-formyl-1-methyl-1,2,4-triazole as an oil. The crude aldehyde was converted to the oxime derivative by mixing 27.3 grams of the aldehyde with 5.1 grams of hydroxylamine hydrochloride, 6.2 grams of sodium bicarbonate, and 100 ml of absolute ethanol and heating the mixture under reflux for 1.5 hours followed by filtering while still hot to give, after recrystallization from ethanol/hexane, 8.3 grams of pure 3-(hydroxyimino)methyl-1-methyl-1,2,4-triazole as colorless plates melting at 195.5° C.

A solution formed of 3.0 grams of the 3-(hydroxyimino)methyl-1-methyl-1,2,4-triazole made above in 20 ml of dry dimethylformamide was treated with 2.96 ml of iodomethane in 40 ml of dry tetrahydrofuran. After stirring under exclusion of light for four days at 35° C., the mixture was filtered to provide 5.41 grams of 1,4-dimethyl-3-(hydroxyimino)methyl-1,2,4-triazolium iodide as a colorless solid melting at 187° C. with decomposition. This salt was ion exchanged in Amberlite Cl− anion exchange resin to give the chloride salt melting at 201°–202° C. with decomposition.

EXAMPLE 2

To a continuously stirred mixture of 13.8 grams of 1,2,4-triazole in 120 ml of methanol cooled at 0° was added 11.9 grams of sodium methoxide. The mixture was allowed to warm to room temperature and stir for 45 minutes whereupon the mixture was again cooled at 0° C. and there was added 25.3 ml of benzyl chloride. After being warmed to room temperature and continuously stirred for 14 hours, the mixture was concentrated and the residue extracted well with dichloromethane. The extract was washed with saturated brine, dried over magnesium sulfate, filtered, and evaporated to give a crude product that was purified by flash column chromatography over silica gel and eluted with dichloromethane/ ethyl acetate (2:1) to give 28.5 grams of pure 1-benzyl-1,2,4-triazole as a solid melting at 44°–45° C.

To a continuously stirred mixture of 0.156 moles of lithium diisopropylamide in 150 ml of THF cooled at −70° C. was added dropwise a solution of 1-benzyl-1,2,4-triazole prepared above in 200 ml of THF. After the mixture was stirred for one hour longer, there was added in one portion 16.5 ml of dry dimethylformamide. The mixture was stirred in the cold for 0.5 hour and then at room temperature for 3.5 hours whereupon there was added dropwise a saturated aqueous solution of 21.5 grams of sodium dihydrogenphosphate. After the mixture was extracted well with dichloromethane, the combined extracts were washed with saturated brine, dried over magnesium sulfate, filtered, and evaporated to give a crude product. The crude product was flash column chromatographed over silica gel and eluted with dichloromethane/ethyl acetate (2:1) to provide 24.6 grams of pure 1-benzyl-3-formyl-1,2,4-triazole as a colorless oil.

The 1-benzyl-3-formyl-1,2,4-triazole was converted to the corresponding oxime derivative, 1-benzyl-3-(hydroxyimino)methyl-1,2,4-triazole, in a manner analogous to that given in Example 1 to yield 23.0 grams of oxime as colorless plates melting at 128°–129° C.

To a solution of 4.50 grams of 1-benzyl-3-(hydroxyimino)methyl-1,2,4-triazole in a mixture of 10 ml of dimethylformamide and 9 ml of THF was added 2.8 ml of iodomethane, and the mixture was stirred at 36° C. for 18 days under exclusion of light. The mixture was then filtered to give 6.4 grams of crude iodide salt which was ion exchanged to provide the chloride salt. Recrystallization of the chloride salt from ethanol/diethyl ether gave 3.6 grams of pure 1-benzyl-3-(hydroxyimino)methyl-4-methyl-1,2,4-triazolium chloride as colorless crystals melting at 147°–147.5° C. with decomposition.

The preceding examples can be repeated with similar success by substituting the generically or specifically prescribed reactants and/or operating conditions of this invention described elsewhere in this specification for those used in the preceding examples.

The following example will serve to illustrate the biological activities of the aldoxime-substituted triazolium derivatives of the invention when tested under in vivo conditions.

EXAMPLE 3

To show the in vivo biological effectiveness of the aldoxime-substituted triazolium compounds of the invention formed Examples 1 and 2 in countering the inactivation of acetylcholinesterase by Soman, a number of mice were treated with twice the lethal dosage ($LD_{50}$) of Soman, where $LD_{50}$ is defined as the dosage at which 50% of the mice injected will die, and then injected intramuscularly with 11.5 milligrams per kilogram of body weight of atropine sulfate.

Some of the mice were then, respectively, injected intramuscularly with varying amounts of the compounds of the invention previously identified herein as preferred compounds 1 and 2 and prepared, respectively, in examples 1 and 2 above. Some of the other mice previously injected with Soman were injected with similar amounts of 2-PAM as a control. The amount of the respective dosages were 1/16, ¼, and ½ of the lethal dosage which is shown in the table as $LD_{50}$, i.e., the dosage amount (in millimoles of the compound per kilogram of body weight of the mouse) at which 50% of the mice injected will die. This amount will vary for each compound and therefore is separately listed in the table for each compound.

The numbers listed in the survival columns are the percentage of ten mice which survived after being treated with the indicated fraction of the lethal dosage of the reactivating treatment agent, i.e., either 2-PAM or one of the aldoxime-substituted triazolium derivatives of the invention. It will be noted that none of the mice treated with 2-PAM, in the amounts listed, survived.

TABLE I

| Sample Compound Number | $LD_{50}$ (millimoles per kg) | Survival Dosage | | |
|---|---|---|---|---|
| | | 1/16 | ¼ | ½ |
| 2-PAM | 0.64 | 0 | 0 | 0 |
| 1 | 6.93 | 0 | 40 | 20 |
| 2 | 14.05 | 0 | 0 | 20 |

EXAMPLE 4

A mixture of 40.0 mmol of pyridine and 40.0 mmol of 2-(methanesulfonyl)ethanol in 25 ml of dichloromethane was added dropwise over a 40 minute period to an ice-cold, continuously stirred mixture of 40.0 mmol of trifluoromethanesulfonic anhydride in 50 ml of dichloromethane. After being stirred for 15 minutes, the mixture was washed with two 50 ml portions of cold water, dried over magnesium sulfate, filtered, and concentrated to give an oil that was passed through a short column of silica gel and eluted with dichloromethane. There was obtained 9.31 grams of pure 2-(methanesulfonyl)ethyl trifluoromethanesulfonate as a colorless oil.

To a stirred suspension of 3.03 grams of 3-(hydroxyimino)methyl-1-methyl-1,2,4-triazole in 75 ml of nitromethane cooled at 0° C. was added a solution of 6.70 grams of 2-(methanesulfonyl)ethyl trifluoromethanesulfonate prepared above in 25 ml of nitromethane. The mixture was allowed to warm to room temperature and stir for 16 hours and then at 30° C. for 10 additional hours. After removing the solvent in vacuo, the remaining residue was Cl− anion exchanged to give a crude product that was recrystallized from ethanol-ethyl acetate to provide 4.98 grams of pure 3-(hydroxyimino)-methyl-1-methyl-4-(2'-methylsulfonyl-1'-ethyl)-1,2,4-trizolium chloride as a colorless, crystalline solid melting at 165°–166° C.

EXAMPLE 5

To show the in vivo biological effectiveness of the aldoxime-substituted triazolium compound of the invention formed in Example 4 above in countering the inactivation of acetylcholinesterase by Soman, a number of mice were treated with twice the lethal dosage ($LD_{50}$) of Soman, where $LD_{50}$ is defined as the dosage at which 50% of the mice injected will die, and then injected intramuscularly with 11.5 milligrams per kilogram of body weight of atropine sulfate as in Example 3.

Some of the mice were then, respectively, injected intramuscularly with varying amounts of preferred compound 3, the compound formed in example 4. Some of the other mice previously injected with Soman were injected with similar amounts of 2-PAM as a control. The amount of the respective dosages were 1/256, 1/32, and ¼ of the lethal dosage which is shown in Table II as $LD_{50}$, i.e., the dosage amount (in millimoles of the compound per kilogram of body weight of the mouse) at which 50% of the mice injected will die.

As in Table I, the numbers listed in the survival columns are the percentage of ten mice which survived after being treated with the indicated fraction of the lethal dosage of the reactivating treatment agent, i.e., either 2-PAM or preferred triazolium compound 3 of the invention. It will be noted again that none of the mice treated with 2-PAM, in the amounts listed, survived.

TABLE II

| Sample Compound Number | $LD_{50}$ (millimoles per kg) | Survival Dosage | | |
|---|---|---|---|---|
| | | 1/256 | 1/32 | ¼ |
| 2-PAM | 0.64 | 0 | 0 | 0 |
| 3 | 1.49 | 0 | 0 | 30 |

Thus, the results indicate that the sample compounds of the invention tested in vivo in mice showed superior results over the 2-PAM control, indicating that the compounds of the invention possess superior capabilities for countering the inactivation of acetylcholinesterase by organophosphorus chemical agents. Similar results have also been obtained in in vivo tests conducted in mice injected with lethal doses of Tabun.

Furthermore, the high amount of the $LD_{50}$ value of the compounds of the invention indicate very low toxicity of the compounds which permits higher dosages to be administered with less risk.

Thus, the invention provides pharmaceutically acceptable low toxicity aldoxime-substituted triazolium compounds which are more effective than standard pyridine-based chemicals in in vivo treatment of acetylcholinesterase inactivated by exposure to toxic organophosphorus chemicals. From the foregoing description, one skilled in the art can easily ascertain the essential features of this invention, and without departing from the spirit and scope thereof, can make various changes and modification of the invention to adapt it to various usages and conditions. All such changes and modification should therefore be deemed to be within the scope of the invention which is limited only by the scope of the following claims.

What is claimed is:

1. A method of countering the inactivation of acetylcholinesterase enzyme in living species poisoned by exposure to an organophosphorus chemical which comprises treating the species in vivo with a therapeutically effective amount of a low toxicity aldoxime-substituted triazolium compound capable of countering said inactivation of said acetylcholinesterase enzyme selected from the class consisting of 1,4-dimethyl-3-(hydroxyimino)methyl-1,2,4-triazolium chloride; 1-benzyl-3-(hydroxyimino)methyl-4-methyl-1,2,4-triazolium chloride; and 3-(hydroxyimino)methyl-1-methyl-4-(2'-methylsulfonyl-1'-ethyl)-1,2,4-triazolium chloride.

2. The method of claim 1 wherein said therapeutically effective amount of said low toxicity compound ranges from 0.05 to 20 grams depending upon the body weight of the living species being treated.

3. The method of claim 1 wherein said therapeutically effective amount of said low toxicity compound ranges from 1/16 to ¼ of the $LD_{50}$ dosage of the compound.

4. A therapeutically effective aldoxime-substituted triazolium compound capable of countering the inactivation of acetylcholinesterase enzyme in living species by organophosphorus chemicals consisting of 1,4-dimethyl-3-(hydroxyimino)methyl-1,2,4-triazolium chloride.

5. A therapeutically effective aldoxime-substituted triazolium compound capable of countering the inactivation of acetylcholinesterase enzyme in living species by organophosphorus chemicals consisting of 1-benzyl-3-(hydroxyimino) methyl-4-methyl-1,2,4-triazolium chloride.

6. A therapeutically effective aldoxime-substituted triazolium compound capable of countering the inactivation of acetylcholinesterase enzyme in living species by organophosphorus chemicals consisting of 3-(hydroxyimino)methyl-1-methyl-4-(2'-methylsulfonyl-1'-ethyl)-1,2,4-triazolium chloride.

* * * * *